United States Patent [19]

Bocion et al.

[11] 4,098,598
[45] Jul. 4, 1978

[54] CYANO CONTAINING BENZOXAZOLINYLIDINES AND USE THEREOF

[75] Inventors: Pierre Bocion, Winterthur; Wijitha de Silva, Schöfflisdorf; Pavol Winternitz, Greifensee, all of Switzerland

[73] Assignee: Hoffmann-La Roche Inc., Nutley, N.J.

[21] Appl. No.: 758,098

[22] Filed: Jan. 10, 1977

Related U.S. Application Data

[62] Division of Ser. No. 559,195, Mar. 17, 1975, Pat. No. 4,028,089.

[30] Foreign Application Priority Data

Mar. 22, 1974 [CH] Switzerland ............... 4038/74

[51] Int. Cl.² ............... C07D 263/56; C07D 295/18; A01N 5/00
[52] U.S. Cl. ............... 71/76; 71/88; 544/137; 260/307 D
[58] Field of Search ............... 260/247.5 EP, 307 D; 544/137; 71/76, 88

[56] References Cited

U.S. PATENT DOCUMENTS 4,028,089  6/1977  Bocion et al. ............... 260/307 D

OTHER PUBLICATIONS

Bocion et al., "Chem. Abstracts", vol. 84 (1976), No. 59434g.

Primary Examiner—Natalie Trousof
Assistant Examiner—R. W. Ramsuer
Attorney, Agent, or Firm—Samuel L. Welt; Bernard S. Leon; George W. Johnston

[57] ABSTRACT

Compounds represented by the formula

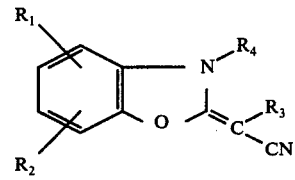

wherein $R_1$ and $R_2$ each are hydrogen or a phenyl; $R_3$ is cyano; $R_5$OCO— in which $R_5$ is a lower alkyl having 1–8 carbons, cycloalkyl having 3–6 carbons, alkenyl having 2–8 carbons, alkynyl having 2–8 carbons or phenyl; $R_6SO_2$- in which $R_6$ is a lower alkyl having 1–8 carbons, cycloalkyl having 3 to 6 carbons or phenyl; $(R_7)(R_8)$NCO— in which $R_7$ and $R_8$ each are hydrogen or a lower alkyl having 1–4 carbons, cycloalkyl having 3–6 carbons, alkenyl having 2–4 carbons or phenyl, or $R_7$ and $R_8$ together with the nitrogen atom to which they are attached are a 3–7 membered ring which may contain a further hetero atom; or $R_9$CO— in which $R_9$ is a lower alkyl having 1–4 carbons, cycloalkyl having 3 to 6 carbons or phenyl; and $R_4$ is hydrogen or a lower alkyl having 1–4 carbons, and salts thereof, having activity which influences plant growth, processes for making such compounds, compositions for using the compounds and methods of using the compounds to influence plant growth are disclosed.

24 Claims, No Drawings

CYANO CONTAINING BENZOXAZOLINYLIDINES AND USE THEREOF

This is a division, of application Ser. No. 559,195 filed Mar. 17, 1975, now U.S. Pat. No. 4,028,089.

DESCRIPTION OF THE INVENTION

The present invention relates to benzoxazoline derivatives having activity which influences plant growth, processes for the manufacture thereof, plant growth regulating compositions containing said benzoxazoline derivatives and methods for treating plants with the active compounds of this invention.

The active compounds provided by the present invention are represented by the formula

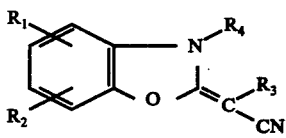

I wherein $R_1$ and $R_2$ each are hydrogen or a phenyl; $R_3$ is cyano; $R_5OCO—$ in which $R_5$ is a lower alkyl having 1-8 carbons, cycloalkyl having 3-6 carbons, alkenyl having 2-8 carbons, alkynyl having 2-8 carbons or phenyl; $R_6SO_2—$ in which $R_6$ is a lower alkyl having 1-8 carbons, cycloalkyl having 3 to 6 carbons or phenyl; $(R_7)(R_8)NCO—$ in which $R_7$ and $R_8$ each are hydrogen or a lower alkyl having 1-4 carbons, cycloalkyl having 3-6 carbons, alkenyl having 2-4 carbons or phenyl, or $R_7$ and $R_8$ together with the nitrogen atom to which they are attached are a 3-7 membered ring which may contain a further hetero atom; or $R_9CO—$ in which $R_9$ is a lower alkyl having 1-4 carbons, cycloalkyl having 3 to 6 carbons or phenyl; and $R_4$ is hydrogen or a lower alkyl having 1-4 carbons,
and salts thereof.

The compounds represented by formula I in which $R_4$ is hydrogen exist in the form of a tautomeric mixture Ia⇌Ib

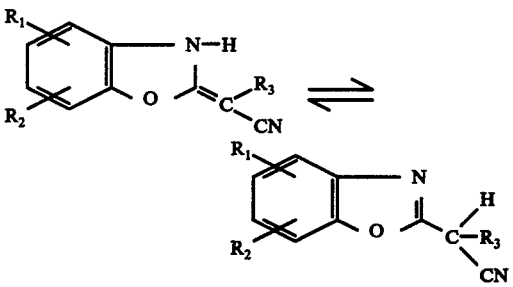

wherein the compounds represented by formula Ia generally predominate.

Both tautomeric forms of the compounds also fall within the scope of the present invention.

The compounds represented by formula I can be made either by (a) reacting a 2-amino-phenol represented by the formula

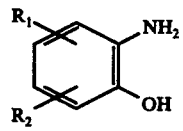

II wherein $R_1$ and $R_2$ have the significance given above, with a 3,3-bis(alkylthio)acrylonitrile represented by the formula

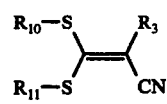

III wherein $R_3$ has the significance given above and $R_{10}$ and $R_{11}$ each are a lower alkyl having 1-4 carbons, The reaction preferably takes place in an inert organic solvent. As the inert organic solvent there can be used not only protic but also aprotic solvents as well as mixtures of such solvents. Especially preferred are low boiling aliphatic alcohols, for example, methanol or ethanol. When $R_3$ is an ester group, i.e., $R_5OCO—$, the solvent used is the alcohol which forms the alcohol component of the ester. This avoids trans-esterification.

The use of basic catalysts accelerates the attainment of the equilibrium of the reaction. For this purpose, most of the conventional basic and inert catalysts are suitable. Particularly suitable catalysts are tertiary organic bases such as triethylamine, N-methylpiperidine, N-methylpyrrolidine, pyridine and the like. It is advantageous to remove continuously the thiol formed during the reaction in order to achieve a reaction which is as complete as possible.

The temperature at which the reaction is carried out can vary within wide limits; i.e., between room temperature and the boiling point of the particular reaction mixture. In order to obtain good yields and pure product, the reaction is preferably carried out at the boiling point of the reaction mixture.

The reaction products, i.e., compounds represented by formula Ia or Ib can be purified by crystallization from a suitable solvent, e.g., dimethyl sulphoxide or dimethylformamide. It is also possible to dissolve these compounds in 2-N aqueous alkali metal hydroxide and to precipitate the compounds from this solution using 2-N aqueous acid.

or (b) lower alkylating a compound represented by formula Ia or I(b). If a salt is desired an acidic compound represented by formula I can be converted into a salt by reaction with a base. The reaction is accomplished by treatment with a lower alkylating agent. For this purpose, the compound is first dissolved in a lower alkanol, e.g., methanol or ethanol, an ether, e.g., dioxane, a di(lower alkyl) ketone, e.g., acetone, dimethylformamide, a chlorinated hydrocarbon, e.g., chloroform, carbon tetrachloride or methylene chloride, an aromatic hydrocarbon, e.g., benzene or water. The preferred solvents are methanol, ethanol, water or mixtures thereof. The resulting solution is treated with the alkylating agent. The alkylating agent used can be any of the usual alkylating agents such as, for example, lower alkyl chlorides, bromides or iodides or di(lower alkyl)sulphates. The alkylation reaction is advantageously carried out at a temperature between 0° and 80° C., preferably at room temperature. The pressure at which the reaction is carried out is not critical; it can be carried out in an open vessel. The preferred starting materials in the alkylation process are the sodium, potassium or ammonium salts of a compound represented by formula Ia or formula Ib.

The compounds represented by formula Ia and Ib are acidic in character and can be converted by reaction with a base into a salt represented by the formula

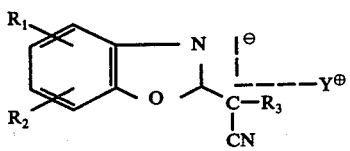

IV wherein $R_1$, $R_2$ and $R_3$ have the significance given earlier and $Y^\oplus$ is the cation of a base.

The manufacture of the salts represented by formula IV can be carried out by conventional means by reacting a compound represented by formula Ia or Ib with a base in water or in a suitable organic solvent, preferably a lower aliphatic alcohol or a mixture thereof with water. When the resulting solution is evaporated, the residue is the salt which, in most cases is a solid water-soluble substance. Preferred bases for the manufacture of the salts of this invention are alkali metal hydroxides, alkaline earth metal hydroxides, primary, secondary and tertiary amines having a straight or branched chain containing 1–12 carbon atoms, cycloalkylamines containing 3–16 carbon atoms, cycloalkyl-alkyl amines containing 3–16 carbon atoms, aralkylamines containing 7–16 carbon atoms or arylamines containing 6–16 carbon atoms, saturated or unsaturated heterocyclic bases. Typical of such amines are, for example, triethylamine, triethanolamine, cyclohexyl(3,7-dimethyloctyl)methylamine, cyclohexyl-dimethylamine, piperidine, N-methylpiperidine, morpholine, N-methylmorpholine and pyridine.

The 2-amino-phenol and 3,3-bis(alkylthio)acrylonitrile starting materials represented by formulas II and III are known compounds and can be prepared according to known methods.

The 3,3-bis(alkylthio)acrylonitriles can be prepared, for example, according to the following reaction scheme from CH-acidic compounds, carbon disulphide and a base, e.g., potassium hydroxide or sodium ethylate via a dithiolate which is subsequently lower alkylated.

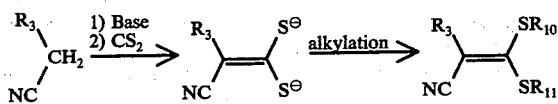

In this reaction scheme $R_3$, $R_{10}$ and $R_{11}$ have the meanings given above.

The expressions "plant growth regulator" or "plant growth influencer" are used interchangeably herein to mean, for example, an active compound which either retards or stimulates the growth of main or side branches or shoots of plants. Such an active compound is capable of influencing, e.g., retarding or stimulating, the formation of flowers, the onset of flowers, the shoot or branch formation, the parthenocarpy, the fruit and-/or leaf fall, the fruit and/or leaf ripening, the transport of substances within the plants, for example, a stimulation of the latex flow and/or of the metabolism or, for example, an increase in the sugar content. The active compounds additionally stabilize the plants against drought and frost and also against substances which are denoted as "atmospheric pollutants" such as, for example, sulphur dioxide, ozone and the like.

For example, in woody plants, e.g., bushes and shrubs, this regulating activity produces a retardation of the growth in height with a simultaneous stimulation of the side growth.

The active compounds of this invention are particularly useful for the regulation of plant growth and have pre-emergence and post-emergent plant growth regulating activity. The compounds are particularly useful as post-emergence plant growth regulators.

The present active compounds are particularly active in and/or against the following plants, particularly young plants:

(a) cereals such as corn, rice, wheat, rye, barley, oats, etc.

(b) wood plants, i.e., trees and shrubs such as fruit trees, e.g., apple, pear, peach, cherry and citrus, cocoa, tea, coffee, banana, gum, olive, walnut, privet, hornbeam, white cedar, juniper, rose, azalea, pyracantha, forsythia, magnolia, (c) ornamental flowering plants such as chrysanthemum, poinsettia, cyclamen, petunia and bromeliad, (d) commercial non-woody field plants such as cotton, tobacco, flax, (e) vegetables such as soya bean, groundnut, sugar beet and pineapple, Solanaceae (tomatoes), legumes, pumpkins, melons, gherkins and the like, (f) berries such as strawberries, bilberries, raspberries, blueberries, blackberries and redcurrants.

Furthermore, the active compounds are useful in vineyards since they reduce the pruning of vines in the vineyards.

In order to provide a uniform distribution of the active compounds of this invention in plant growth regulating compositions, the compounds are mixed with conventional adjuvants, modifiers, diluents or conditioning agents customary in plant growth regulating agents and the mixture obtained is formulated to provide solutions, emulsions, emulsifiable concentrates, dispersions, dusts, granulates or wettable powders.

Plant growth regulating compositions in the form of liquid formulations for direct spraying can be prepared, for example, in the form of aqueous solutions or as solutions in solvent mixtures which contain, for example, acetone, methanol and dimethylformamide in a ratio of 90:8:2 (volume/volume).

Emulsifiable concentrates which contain 25–50% or more of one or more of the active compounds of this invention, depending on the solubility thereof, can be prepared using suitable solvents, e.g., N-methylpyrrolidine, dimethylformamide and the like. Conventional surface-active agents, e.g., wetting agents, dispersants, emulsifiers and the like are added in a sufficient amount to produce a formulation having the desired characteristics.

Various application forms can be better adapted to the numerous purposes for which the active compounds can be used if substances which improve the dispersion, adhesion, penetration and resistance to rain are added. Such substances are conventional and include fatty acids, waxes, resins, wetting agents, emulsifiers, mineral oils, vegetable oils, binding agents and the like. In a similar manner, the biological spectrum of the compositions containing the active compounds can be greatly broadened by the addition of substances having bactericidal, herbicidal or fungicidal properties or by the addition of fertilizers, chelate forming agents and other plant growth regulators.

Examples of herbicides and plant growth regulators which can be present in the compositions provided by the present invention are:
2,2-dichloropropionic acid,
N-(4-aminobenzenesulphonyl)methylcarbamate,
2-chloro-4-ethylamino-6-isopropylamino-1,3,5-triazine,
4-chloro-2-oxobenzothiazolin-3-yl-acetic acid,
5-bromo-6-methyl-3-(1-methyl-n-propyl)uracil,
3,5-dibromo-4-hydroxybenzonitrile,
D,N-ethyl-2-(phenylcarbamoyloxy)propionamide,
N-(4-bromo-3-chlorophenyl)-N'-methoxy-N'-methylurea,
methyl-2-chloro-9-hydroxyfluorene-9-carboxylate,
N'-4-(4-chlorophenoxy)-phenyl-N,N-dimethylurea,
isopropyl-N-(3-chlorophenyl)-carbamate,
2,3,5,6-tetrachloroterephthalic acid dimethylester (DCPA),
2,4-dichlorophenoxyacetic acid,
4-isopropylamino-6-methylamino-2-methylthio-1,3,5-triazine,
n-butyl 9-hydroxyfluorene-9-carboxylate,
ethylene,
naphthoxyacetic acid,
3,6-dichloro-2-methoxybenzoic acid,
(±)-2-(2,4-dichlorophenoxy)propionic acid,
9,10-dihydro-8a,10a-diazoniaphenanthrene-2A,
N'-(3,4-dichlorophenyl)-N,N-dimethylurea,
gibberellic acid,
indolylacetic acid,
indolylbutyric acid,
4-hydroxy-3,5-diiodobenzonitrile,
N'-(3,4-dichlorophenyl)-N-methoxy-N-methylurea,
(4-chloro-2-methylphenoxy)acetic acid,
4-(4-chloro-2-methylphenoxy)butyric acid,
(±)-2-(4-chloro-2-methylphenoxy)propionic acid,
N-(benzothiazol-2-yl)-N',N'-dimethylurea,
N'-(3-chloro-4-methoxyphenyl)-N,N-dimethylurea,
1,2,3,6-tetrahydro-3,6-dioxopyridazine,
N'-(4-chlorophenyl)-N-methoxy-N-methylurea,
N'-(4-chlorophenyl)-N,N-dimethylurea,
naphthylacetic acid,
N-1-naphthylphthalamic acid,
2,4-dichlorophenyl 4-nitrophenyl ether,
1,1'-dimethyl-4,4'-bipyridylium-2A,
3-(m-tolylcarbamoyloxy)phenyl carbamate,
4-amino-3,5,6-trichloropicolinic acid,
4,6-bis-isopropylamino-2-methylthio-1,3,5-triazine,
N-(3,4-dichlorophenyl)propionamide,
isopropyl-N-phenylcarbamate,
5-amino-4-chloro-2-phenylpyridazin-3(2H)-one
N-dimethylaminosuccinic acid,
2-chloroethylphosphorous acid,
tributyl-2,4-dichlorobenzyl-phosphonium chloride,
2,4,5-trichlorophenoxypropionic acid,
2,3,6-trichlorobenzoic acid,
2-chloro-4,6-bis-ethylamino-1,3,5-triazine,
sodium chloroacetate,
2,4,5-trichlorophenoxyacetic acid,
5-chloro-6-methyl-3-tert.butyluracil,
4-ethylamino-2-methylthio-6-tert.butylamino-1,3,5-triazine-(tert.butryn),
2,3,5-triiodobenzoic acid and
1,14-trimethyl-6-isopropyl-5-propionyl-indane.

Examples of fungicides which can be present in the compositions provided by the present invention are:
2,4-dichloro-6-(o-chloroaniline)-S-triazine,
2,4,5,6-tetrachloroisophthalic acid nitrile,
p-dimethylaminophenyldiazo sodium sulphonate,
1,4-dichloro-2,5-dimethoxybenzene,
manganese ethylene-bis-dithiocarbamate,
zinc ethylene-bis-dithiocarbamate,
coordination product from zinc and manganese ethylene-bis-dithiocarbamate,
methyl-1-(butylcarbamoyl)-2-benzimidazole carbamate,
2-(4-thiazole)-benzimidazole and
cis-N-[(trichloromethyl)-thio]-4-cyclohexene-1,2-dicarboximide.

The amounts of active compound which can be used may be determined based on the test results set forth hereinafter. However, it will be appreciated that these amounts can be modified to take into account numerous other factors not involved in the test and which might influence the amounts used. For example, the amount can vary not only between different species of plants but also within a particular species, depending on factors such as the size and age of the plant, the particular active compound used, the time of year, the type of soil and climatic conditions at the time of use such as air temperature, light intensity, rain and wind. Further, if the active compounds come into contact with the plants via the soil, higher concentrations will be necessary since, with this type of use, the plant is indirectly treated in comparison with a direct treatment by application of the active compound on to leaves and stems, e.g., by spraying. Therefore the amount of active compound effective to influence plant growth in the desired manner is empirical.

Accordingly, the amount of active compound present in the compositions varies depending on the plants to be controlled, the amount required for application, the method of application, the particular active compound used and the degree of regulation of plant growth which is desired. In general, the present compositions contain less than 50% by weight of active compound in a ready-for-use spray form.

In principle, the amount of active compound which is used is chosen so that an effective control of the plant growth is achieved. Accordingly, the choice of the minimum amount of active compound is determined by the minimum amount of such compound which is able to effect the lowest limit of growth retardation desired. The choice of the maximum amount of active compound used is correspondingly determined by that amount of such compound which is able to bring about the upper limit of growth retardation desired. In the case of tomato plants, the criteria for an effective growth retardation for tomato plants are of such a nature that a dwarfed plant which has no loss in fruit quality or quantity is particularly desired. The parameters for an effective growth regulating activity in such plants are retarded growth in height and increased or nonretarded side-growth as a minimum effect and retarded growth in height and retarded side-growth as a maximum effect. The amount of active compound corresponding to these criteria or bringing them about is determined by such aspects, for example, of the tomato plant. In order to achieve the greatest post-emergence growth regulating activity, amounts of about 0.01 kg. to about 10 kg., or more if required, per hectare are used, these amounts being based on the weight of the active compound. The preferred post-emergence growth regulating activity is generally achieved using amounts of active compound which lie between about 0.05 kg. and about 1 kg. of active compound per hectare. If a spray composition is used to apoly the active compound, a preferred range of active compound in the spray composition lies between 10 parts per million and 100,000 parts per million of composition depending on the plant species to be treated and the particular active compound used. An especially preferred amount generally lies between about 50 parts per million and 1000 parts per million.

A further advantage of the present active compounds lies in the absence of both a lasting effect on the plants or a regulating activity which remains in the soil. The present compounds decompose slowly and gradually lose their activity. This effect has advantages since (a) a short-term effect which may be lengthened by subsequent further treatment is produced;
(b) the normal growth behavior of the plant reoccurs in step with the decrease in activity; and
(c) no ecologically harmful residues remain either on the plant or in the soil.

The duration of the retardation effect varies according to the active compound used and other factors such as the type of plant treated, climatic conditions and the like.

Although the active compounds provided by the present invention possess a plant growth regulating activity, they are virtually non-toxic to animals.

It will, of course, be appreciated that not all of the active compounds of this invention are active against all plants. Each of the compounds does, however, possess activity against a specific plant or plants and this activity is a function of the particular compound. As will be evident from the following, a particular advantage of the present invention is that the plant growth regulating compounds possess pre-emergence and post-emergence plant growth regulating activity when used for the treatment of various plants, the range of plants being extremely wide. The growth regulating activity of the present active compounds will be evident from the following tests for the determination of the post-emergence activity.

Several concentrations of active compounds sprayed on to the plant so that a complete spray coating is obtained or the roots are watered with just sufficient solution containing active compound for the pot in which the plant is standing to hold without liquid being drained into the subsoil (the amount required is determined previously in a blind test using water).

For example, gherkins of the variety "Chinese serpent" in the 8-10 leaf state are treated with concentrations of 0.05 or 0.15 kg/ha of 2-benzoxazolinylidene-malononitrile formulated as a wettable powder of the following composition:

| 2-Benzoxazolinylidene-malononitrile | 50.0% |
|---|---|
| Tensiofix LX spec.[1] | 3.5% |
| Tensiofix BCZ[2] | 2.0% |
| Kaolin B 24[3] | 44.5% |

[1]Mixture of non-ionic alkylphenol derivatives, polyethyleneoxidealkylphenol condensation products and anionic dodecylbenzenesulphonates available from Tensra SA, Avenue des Tilleuils 62, B-4000 Liege.
[2]Alkylsulphonates available from Tensra
[3]Kaolin clay available from Societe Argiles et Mineraux SA Clerac, France.

For this purpose, the wettable powder is dispersed in water and 1,000 l/ha of this dispersion are sprayed. This means that using the formulation above 100 g. or 300 g. of wettable powder containing 50 g. or 150 g. of active compound are dispersed in 1000 liters of water and are applied to 1 ha.

The results, which are given in Table 1, show the increase in yield of the treated plants as compared with untreated controls. The yield of the untreated controls is arbitrarily indicated as 100%.

Table 1

| Active Compound | Concentration kg. Active Substance/ha | Yield in % |
|---|---|---|
| 2-Benzoxazolinylide-malononitrile | 0.05 | 156 |
|  | 0.15 | 252 |
| None | — | 100 |

In another test, buckwheat (Fagopyrum vulg.) is treated with a spray mixture containing 1% by weight of active compound, 2.5% of kaolin and 96.5% of water. 1000 l/ha (10 kg. of test compound per ha) are sprayed so that a complete spray covering is achieved.

Two weeks after the treatment the results are evaluated by recording the deformation (effect 1) and necrosis (effect 2) in percent based on untreated controls in which the deformation and necrosis amounts to 0%. In order to record the growth disturbance, variation of the buds, leaves and stems are taken as a basis. The results are compiled in Table 2.

Table 2

| Active Compound | Effect 1 in % | Effect 2 in % |
|---|---|---|
| 2-Benzoxazolinylidene-cyanoacetic acid methyl ester | 30 | 20 |
| (5-Phenyl-2-benzoxazolinylidene)-malononitrile | 0 | 20 |
| 2-Benzoxazolinylidene-phenylsulphonyl-acetonitrile | 30 | 80 |
| 3-Methyl-benzoxazolinylidene-malonitrile | 20 | 0 |
| 2-Benzoxazolinylidene-cyanoacetic acid anilide | 0 | 30 |
| 2-Benzoxazolinylidene-cyanoacetic acid | 30 | 30 |
| 2-Benzoxazolinylidene-benzoylacetonitrile | 60 | 0 |
| 2-Benzoxazolinylidene-cyanoacetic acid butyl ester | 20 | 0 |
| 2-Benzoxazolinylidene-cyanoacetic acid cyclohexyl ester | 10 | 0 |
| 2-Benzoxazolinylidene-cyanoacetic acid allyl ester | 30 | 10 |
| 2-Benzoxazolinylidene-cyanoacetic acid propargyl ester | 30 | 10 |
| 2-Benzoxazolinylidene-cyanoacetic acid phenyl ester | 20 | 0 |
| 2-Benzoxazolinylidene-cyanoacetic acid N-dimethylamide | 30 | 10 |
| 2-Benzoxazolinylidene-cyanoacetic acid N-cyclohexylamide | 30 | 10 |
| 2-Benzoxazolinylidene-cyanoacetic acid morpholide | 40 | 20 |
| 2-Benzoxazolinylidene-cyanoacetic acid N-propylamide | 30 | 0 |
| 2-Benzoxazolinylidene-malononitrile | 30 | 20 |
| 2-Benzoxazolinylidene-malononitrile triethylammonium salt | 30 | 30 |
| 2-Benzoxazolinylidene-malononitrile cyclohexyl-(3,7-dimethyloctyl)-methyl ammonium salt | 30 | 80 |
| 2-Benzoxazolinylidene-malononitrile triethanolammonium salt | 40 | 20 |
| 2-Benzoxazolinylidene-malononitrile ammonium salt | 0 | 50 |
| 2-Benzoxazolinylidene-malononitrile sodium salt | 0 | 60 |
| 2-Benzoxazolinylidene-malononitrile potassium salt | 0 | 50 |
| Control | 0 | 0 |

In a further experiment, the number of flowers and ripe fruits on "black nightshade" (Solanum nigrum) is determined. For this purpose, the plants are sprayed to saturation with a concentration of 500 parts per million and 1000 parts per million of active compound. After 6 weeks, the number of flowers and, simultaneously, also the number of ripe fruits per plant is determined by counting. The results are compiled in Table 3, each value being an average of 5 plants.

Table 3

| Active Compound | Number of Flowers Concentration | | Number of Ripe Fruits Concentration | |
|---|---|---|---|---|
| | 1000 ppm | 500 ppm | 1000 ppm | 500 ppm |
| 2-Benzoxazolinylidene-malononitrile | 36.6 | 33.8 | 3.6 | 2.8 |
| 2-Benzoxazolinylidene-malononitrile triethanolammonium salt | 34.4 | 29.6 | 1.4 | 3.8 |
| 2-Benzoxazolinylidene-malononitrile ammonium salt | 34.6 | 40.6 | 3.8 | 1.2 |
| 2-Benzoxazolinylidene-cyanoacetic acid methyl ester | 27.6 | 28.2 | 5.4 | 4.8 |
| Control | 25.6 | | 2.8 | |

It will accordingly be appreciated that this invention includes within its scope:
(a) a plant growth regulating or influencing composition which contains an effective amount of one or more of the active compounds hereinbefore defined in association with a compatible carrier material;
(b) a method for regulating plant growth, which method comprises treating the plants whose growth is to be regulated with an effective growth regulating amount of active compound or with an amount of a composition containing sufficient active compound to regulate plant growth.

The following Examples illustrate the process provided by the present invention.

EXAMPLE 1

8.5 g. (0.05 M) of 3,3-bis(methylthio)-2-cyanoacrylonitrile and 6.0 g. (0.055 M) of 2-aminophenol in 200 ml. of methanol or ethanol are held under reflux for 4 hours, subsequently evaporated to dryness in vacuo and the resulting residue is made into a paste with 20 ml. of methanol or ethanol. The resulting crystals are filtered off under suction, washed with 10 ml. of ethanol and dried. There is obtained crude 2-benzoxazolinylidene-malononitrile of melting point ca. 240°–300° C. (dec.).

For purification, the product can be dissolved in 60 ml. of hot dimethylformamide and the hot solution treated with 30 ml. of water to give 2-benzoxazolinylidene-malononitrile. Alternatively, the product can be dissolved in 100 ml. of aqueous 2-N sodium hydroxide, filtered and the desired product precipitated from the filtrate with 100 ml. of 2-N hydrochloric acid.

EXAMPLE 2

The procedure described in Example 1 is repeated using, instead of 2-aminophenol, an equivalent amount of 2-amino-4-phenylphenol in ethanol and holding the mixture under reflux in the presence of 1 ml. of trimethylamine for 60 hours. The crude product is crystallized from acetone to obtain (5-phenyl-2-benzoxazolinylidene)malononitrile of melting point ca. 236° C. (dec.).

EXAMPLE 3

The procedure described in Example 1 is repeated using, instead of 3,3-bis(methylthio)-2-cyanoacrylonitrile, an equivalent amount of 3,3-bis(methylthio)-2-cyanoacrylic acid methyl ester. There is obtained 2-benzoxazolinylidene-cyanoacetic acid methyl ester of melting point 270°–273° C. (dec.) (from methanol).

EXAMPLE 4

The procedure described in Example 1 is repeated using, instead of 3,3-bis(methylthio)-2-cyanoacrylonitrile, an equivalent amount of 3,3-bis(methylthio)-2-cyanoacrylic acid butyl ester in butanol. There is obtained 2-benzoxazolinylidene-cyanoacetic acid butyl ester of melting point 116°–119° C. [from ethyl acetate/hexane (1:4)].

3,3-bis(methylthio)-2-cyanoacrylic acid butyl ester can be prepared as follows:

34.9 g. (0.8 M) of a 55% suspension of sodium hydride are washed with absolute benzene and suspended in 1000 ml. of benzene and, while stirring, 56.4 g. (0.4 M) of cyanoacetic acid butyl ester are added dropwise at 25° C. over a period of 2 hours. Subsequently, 30.4 g. (0.4 M) of carbon disulfide are added, the mixture is stirred at 25° C. for 20 hours. 113.5 g. (0.8 M) of methyl iodide are added dropwise over a period of 1 hour and the resulting mixture is heated to reflux for 1 hour. The resulting mixture is extracted three times with 500 ml. of aqueous 2-N sodium hydroxide each time, washed neutral, dried and evaporated.

41.9 g. of the resulting crude product were purified by chromatography on silica gel to obtain 3,3-bis(methylthio)-2-cyanoacrylic acid butyl ester as a viscous oil.

EXAMPLE 5

The procedure described in Example 1 is repeated using, instead of 3,3-bis(methylthio)-2-cyanoacrylonitrile, an equivalent amount of 3,3-bis(methylthio)-2-phenylsulfonylacrylonitrile and holding the mixture under reflux for 34 hours to obtain 2-benzoxazolinylidene-phenylsulfonylacetonitrile having a melting point of 215°–217.5° C. (from ethanol).

3,3-bis(methylthio)-2-phenylsulfonyl-acrylonitrile can be prepared as follows:

15.2 g. (0.2 M) carbon disulfide are added to a solution of 16.0 g. (0.4 M) sodium hydroxide and 36.2 g. (0.2 M) phenylsulfonylacetonitrile in 500 ml. water, with stirring at 25° C. After three hours of intensive stirring 55.5 g. (0.44 M) of dimethylsulfate was added over a period of one and one half hours at 10°–15° C. The resulting crystals were filtered with suction, washed with water, and at the conclusion with a little ethanol and dried to obtain 3,3-bis(methylthio)-2-phenylsulfonylacrylonitrile melting at 99°–101° C., and at 108°–110° C. from methylene chloride/hexane.

EXAMPLE 6

The procedure described in Example 1 is followed using, instead of 3,3-bis(methylthio)-2-cyanoacrylonitrile, an equivalent amount of 3,3-bis(methylthio)-2-benzoylacrylonitrile and holding the mixture under reflux for 2 hours to obtain 2-benzoxazolinylidene-benzoylacetonitrile of melting point 207°–208° C. (from methanol).

EXAMPLE 7

The procedure described in Example 1 is repeated using, instead of 3,3-bis(methylthio)-2-cyanoacrylonitrile, an equivalent amount of 3,3-bis(methylthio)-2-cyanoacrylamide and holding the mixture under reflux for 12 hours to obtain 2-benzoxazolinylidene-cyanoacetic acid amide of melting point 220°–222° C. (dec.) (from methanol).

EXAMPLE 8

The procedure described in Example 1 is repeated using, instead of 3,3-bis(methylthio)-2-cyanoacrylonitrile, an equivalent amount of 3,3-bis(methylthio)-2-cyanoacrylanilide and holding the mixture under reflux for 9 hours. The resulting mixture is evaporated to dryness in vacuo, dissolved in 200 ml. of methanol and heated to boiling for a further 3 hours to obtain 2-benzoxazolinylidene-cyanoacetic acid anilide of melting point 231°–233° C. (from methanol).

EXAMPLE 9

9.15 g. (0.05 M) of 2-benzoxazolinylidene-malononitrile and 16.0 g. (0.4 M) of sodium hydroxide are dissolved in 500 ml. of water. The solution is brought to 5° C. while stirring and, over a period of 1 hour, 25.2 g. (0.2 M) of dimethyl sulfate are added dropwise. The resulting crystals are filtered off under suction, washed with water and dried to obtain 3-methyl-benzoxazolinylidene-malononitrile of melting point 198°–200° C.

EXAMPLE 10

1.8 g. (0.01 M) of 2-benzoxazolinylidene-malononitrile and 0.4 g. (0.01 M) of sodium hydroxide are dissolved in 35 ml. of a methanol/water mixture (6:1), made neutral with a small excess of 2-benzoxazolinylidene-malononitrile, any undissolved starting material is filtered off and the clear solution is evaporated to dryness in vacuo to obtain 2-benzoxazolinylidene-malononitrile sodium salt in the form of a colorless powder (melting point >300° C.) which has a very good solubility in water and methanol.

EXAMPLE 11

The procedure described in Example 10 is repeated using, instead of sodium hydroxide, an equivalent amount of potassium hydroxide in water at 60° C. to obtain 2-benzoxazolinylidene-malononitrile potassium salt of melting point >300° C.

EXAMPLE 12

The procedure described in Example 10 is repeated using, as the base, an equivalent amount of an aqueous ammonia solution in methanol. The solution is evaporated, the residue dissolved in 20 ml. of methanol and treated with 100 ml. of benzene. The resulting crystals are filtered off under suction, washed with benzene and dried to obtain 2-benzoxazolinylidene-malononitrile ammonium salt of melting point 240°–275° C. (dec.) which is less soluble in water than the sodium or potassium salts, but which has a good solubility in methanol.

EXAMPLE 13

The procedure described in Example 10 is repeated using, as the base, an equivalent amount of triethanolamine in 30 ml. of methanol. The resulting viscous oil solidifies after several days. The crystalline mass is made into a paste with 50 ml. of ether and the resulting crystals are filtered off under suction, washed with ether and dried to obtain 2-benzoxazolinylidene-malononitrile triethanolammonium salt of melting point 97°–100° C.

EXAMPLE 14

The procedure described in Example 10 is repeated using, as the base, an equivalent amount of triethylamine in 30 ml. of methanol to obtain 2-benzoxazolinylidene-malononitrile triethylammonium salt in the form of a viscous oil ($n_D^{20}$ = 1.5772) which could not be crystallized.

EXAMPLE 15

The procedure described in Example 10 is repeated using, as the base, an equivalent amount of cyclohexyl-(3,7-dimethyloctyl)-methylamine in 80 ml. of methanol to obtain 2-benzoxazolinylidene-malononitrile cyclohexyl-(3,7-dimethyloctyl)-methylammonium salt in the form of a viscous oil which is only slightly soluble in water, but which has a good solubility in 50% methanol.

EXAMPLE 16

The procedure described in Example 1 is repeated using, instead of 3,3-bis(methylthio)-2-cyanoacrylonitrile, an equivalent amount of 3,3-bis(methylthio)-2-cyanoacrylic acid phenyl ester in ethanol to obtain 2-benzoxazolinylidene-cyanoacetic acid phenyl ester of melting point 236°–237° C. (dec.) (from acetone).

3,3-bis(methylthio)-2-cyanoacrylic acid phenyl ester can be prepared in a manner analogous to that described in Example 4 from cyanoacetic acid phenylester carbon disulfide and methyl iodide. 1,2-Dimethoxyethane is used as the solvent. After completion of the reaction, the solvent is distilled off in vacuo, the residue dissolved in 500 ml. of methylene chloride and shaken out four times with 500 ml. of water each time. After drying the methylene chloride phase over sodium sulfate and distillation of the solvent, there is obtained, crude 3,3-bis(methylthio)-2-cyanoacrylic acid phenyl ester which is purified by crystallization; melting point 75°–76° C. [from methylene chloride/hexane (1:3)].

EXAMPLE 17

The procedure described in Example 1 is repeated using, instead of 3,3-bis(methylthio)-2-cyanoacrylonitrile, an equivalent amount of 3,3-bis(methylthio)-2-cyanoacrylic acid cyclohexyl ester in 100 ml. of dimethyl sulfoxide and holding the reaction for 12 hours at 130° C. The resulting mixture is poured into 500 ml. of water and extracted four times with 200 ml. of ether each time. The combined ether extracts are washed with water, dried over sodium sulfate and evaporated to obtain 2-benzoxazolinylidene-cyanoacetic acid cyclohexyl ester of melting point 143°–145° C. [from ethyl acetate/ether (1:3)].

3,3-bis(methylthio)-2-cyanoacrylic acid cyclohexyl ester is prepared in a manner analogous to that described in Example 4 from cyanoacetic acid cyclohexyl ester, carbon disulfide and methyl iodide. The crude product is fractionated in a vacuum to obtain a viscous oil of boiling point 157°–159°/0.04 Torr.

EXAMPLE 18

The procedure described in Example 1 is repeated using, instead of 3,3-bis(mehtylthio)-2-cyanoacrylonitrile, an equivalent amount of 3,3-bis(methylthio)-2-cyanoacrylic acid allyl ester in 100 ml. of allyl alcohol and holding the mixture under reflux for 7 hours to obtain 2-benzoxazolinylidene-cyanoacetic acid allyl ester of melting point 181°–183° C. (from ethyl acetate).

3,3-bis(methylthio)-2-cyanoacrylic acid allyl ester is prepared in a manner analogous to that described in Example 4 from cyanoacetic acid alkyl ester, carbon disulfide and methyl iodide. The crude product is fractionated in a vacuum to obtain a viscous oil; boiling point 125°–132° C./0.04 Torr; melting point 36°–37.5° C.

EXAMPLE 19

The procedure described in Example 1 is repeated using, instead of 3,3-bis(methylthio)-2-cyanoacrylonitrile, an equivalent amount of 3,3-bis(methylthio)-2-cyanoacrylic acid propargyl ester in 100 ml. of propargyl alcohol and holding the mixture under reflux for 2 hours to obtain 2-benzoxazolinylidene-cyanoacetic acid propargyl ester of melting point 258°–259° C. (decomposition) (from acetone).

3,3-bis(methylthio)-2-cyanoacrylic acid propargyl ester is prepared in a manner analogous to that described in Example 4 from cyanoacetic acid propargyl ester, carbon disulfide and methyl iodide. 1,2-Dimethoxyethane is used as the solvent. After completion of the reaction, the solvent is distilled off in vacuo, the residue dissolved in 500 ml. of methylene chloride and shaken out four times with 500 ml. of water each time. The crude product obtained after drying the organic phase over sodium sulphate and distillation of the solvent, is purified by crystallization; melting point 77°–79° C. [from methylene chloride/hexane (1:3)].

EXAMPLE 20

The procedure described in Example 1 is repeated using, instead of 3,3-bis(methylthio)-2-cyanoacrylonitrile, an equivalent amount of 3,3-bis(methylthio)-2-cyanoacrylic acid morpholide and holding the mixture under reflux for 24 hours to obtain 2-benzoxazolinylidene-cyanoacetic acid morpholide of melting point 217°–219° C. (from ethanol).

3,3-bis(methylthio)-2-cyanoacrylic acid morpholide is prepared in a manner analogous to that described in Example 4 cyanoacetic acid morpholide, carbon disulfide and methyl iodide.
1,2-Dimethoxyethane is used as the solvent. After completion of the reaction, the solvent is distilled off in vacuo, the residue dissolved in 500 ml. of methylene chloride and shaken out four times with 500 ml. of water each time. The crude product obtained after drying the organic pahse and distillation of the solvent, is purified by chromatography on silica gel to obtain an oil which solidifies to crystals after standing for a considerable time; melting point 55°–57° C.

EXAMPLE 21

The procedure described in Example 1 is repeated using, instead of 3,3-bis(methylthio)-2-cyanoacrylonitrile, an equivalent amount of 3,3-bis(methylthio)-2-cyano-N-cyclohexyl-acrylamide and holding the mixture under reflux for 12 hours to obtain 2-benzoxazolinylidene-cyanoacetic acid N-cylcohexylamide of melting point 185°–187° C. (from ethyl acetate).

3,3-Bis(methylthio)-2-cyano-N-cyclohexyl-acrylamide is prepared in a manner analogous to that described in Example 4 from cyanoacetic acid-N-cyclohexyl-amide, carbon disulfide and methyl iodide.
1,2-Dimethoxyethane is used as the solvent. After completion of the reaction, the solvent is distilled off, the residue dissolved in 500 ml. of methylene chloride and shaken out five times with 500 ml. of water each time. The crude product obtained after drying the organic phase and distillation of the solvent, is purified by crystallization; melting point 103°–105° C. (from ethyl acetate).

EXAMPLE 22

The procedure described in Example 1 is repeated using, instead of 3,3-bis(methylthio)-2-cyanoacrylonitrile, an equivalent amount of 3,3-bis(methylthio)-2-cyano-N,N-dimethyl-acrylamide and holding the mixture under reflux for 12 hours to obtain 2-benzoxazolinylidene-cyanoacetic acid N,N-dimethylamide of melting point 196° C. (from ethyl acetate).

3,3-Bis(methylthio)-2-cyano-N,N-dimethyl-acrylamide is prepared in a manner analogous to that described in Example 4 from cyano-acetic acid-N-dimethyl-amide, carbon disulfide and methyl iodide.
1,2-Dimethoxyethane is used as the solvent. After completion of the reaction, the solvent is distilled off, the residue dissolved in 500 ml. of methylene chloride and shaken out four times with 500 ml. of water each time. The crude product obtained after drying the organic phase and distillation of the solvent, is purified by chromatography on silica gel to obtain an oil which solidifies to crystals after standing for a consdierable time; melting point 45°–46° C.

EXAMPLE 23

The procedure described in Example 1 is repeated using, instead of 3,3-bis(methylthio)-2-cyanoacrylonitrile, an equivalent amount of 3,3-bis(methylthio)-2-cyano-N-propylacrylamide and holding the mixture under reflux for 12 hours to obtain 2-benzoxazolinylidene-cyanoacetic acid N-propylamide of melting point 215°–220° C. (from ethyl acetate).

3,3-Bis(methylthio)-2-cyano-N-propyl-acrylamide is prepared in a manner analogous to that described in Example 4 from cyanoacetic acid propylamide, carbon disulfide and methyl iodide.
1,2-Dimethoxyethane is used as the solvent. After completion of the reaction, the solvent is distilled off, the residue dissolved in 500 ml. of methylene chloride and shake out four times with 500 ml. of water each time. After drying the organic phase and sitillation of the solvent, there is obtained the crude product which is purified by crystallization; melting point 65°–66° C. (from ethyl acetate/hexane).

We claim:
1. Compounds represented by the formula

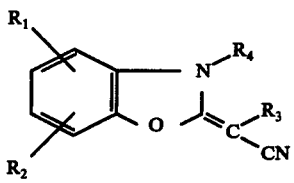 (I)

wherein $R_1$ and $R_2$ each are hydrogen or a phenyl; $R_3$ is $R_5O-CO-$ in which $R_5$ is a lower alkyl having 1–8 carbons, cycloalkyl having 3–6 carbons, alkenyl having 2–8 carbons, alkynyl having 2–8 carbons or phenyl; $R_6SO_2-$ in which $R_6$ is a lower alkyl having 1–8 carbons, cycloalkyl having 3 to 6 carbons or phenyl; $(R_7)(R_8)NCO-$ in which $R_7$ and $R_8$ each are hydrogen or a lower alkyl having 1–4 carbons, cycloalkyl having 3–6 carbons, alkenyl having 2–4 carbons or phenyl, or $R_7$ and $R_8$ together with the nitrogen atom to which they are attached form a morpholine ring; or $R_9CO-$ in which $R_9$ is a lower alkyl having 1–4 carbons, cycloalkyl having 3 to 6 carbons or phenyl; and $R_4$ is hydrogen or a lower alkyl having 1–4 carbons, and salts thereof.

2. A compound according to claim 1, 2-benzoxazolinylidene-cyanoacetic acid methyl ester.

3. A compound according to claim 1, 2-benzoxazolinylidene-cyanoacetic acid butyl ester.

4. A compound according to claim 1, 2-benzoxazolinylidene-phenylsulfonylacetonitrile.

5. A compound according to claim 1, 2-benzoxazolinylidene-benzoylacetonitrile.

6. A compound according to claim 1, 2-benzoxazolinylidene-cyanoacetic acid amide.

7. A compound according to claim 1, 2-benzoxazolinylidene-cyanoacetic acid anilide.

8. A compound according to claim 1, 2-benzoxazolinylidene-cyanoacetic acid phenyl ester.

9. A compound according to claim 1, 2-benzoxazolinylidene-cyanoacetic acid cyclohexyl ester.

10. A compound according to claim 1, 2-benzoxazolinylidene-cyanoacetic acid allyl ester.

11. A compound according to claim 1, 2-benzoxazolinylidene-cyanoacetic acid propargyl ester.

12. A compound according to claim 1, 2-benzoxazolinylidene-cyanoacetic acid morpholide.

13. A compound according to claim 1, 2-benzoxazolinylidene-cyanoacetic acid N-cyclohexylamide.

14. A compound according to claim 1, 2-benzoxazolinylidene-cyanoacetic acid N,N-dimethylamide.

15. A compound according to claim 1, 2-benzoxazolinylidene-cyanoacetic acid N-propylamide.

16. A plant growth regulating composition containing as the active ingredient, a plant growth regulating effective amount of one or more of the compounds of claim 1 and an agriculturally acceptable compatible carrier.

17. A composition according to claim 16 containing as an active ingredient 2-benzoxazolinylidene-cyanoacetic acid methyl ester.

18. A composition according to claim 16 containing as an active ingredient 2-benzoxazolinylidene-cyanoacetic acid butyl ester.

19. A composition according to claim 16 containing as an active ingredient 2-benzoxazolinylidene-phenylsulfonylacetonitrile.

20. A composition according to claim 16 containing as an active ingredient 2-benzoxazolinylidene-benzoylacetonitrile.

21. A composition according to claim 16 containing as an active ingredient 2-benzoxazolinylidene-cyanoacetic acid amide.

22. A composition according to claim 16 containing as an active ingredient 2-benzoxazolinylidene-cyanoacetic acid anilide.

23. A plant growth regulating composition comprising a mixture consisting of approximately 4 parts to approximately 16 parts by weight of one or more of the compounds of claim 1.

24. A method for the regulation of plant growth, which method comprises treating the plants whose growth is to be regulated with a plant growth regulating amount of a composition containing as the active ingredient a compound of claim 1.

* * * * *